(12) United States Patent
Park et al.

(10) Patent No.: US 8,329,457 B2
(45) Date of Patent: Dec. 11, 2012

(54) BIOARTIFICIAL LIVER SYSTEM USING BIOREACTOR PACKED WITH GEL BEADS

(75) Inventors: Jung Keug Park, Seoul (KR); Sung Koo Kim, Busan (KR); Suk Koo Lee, Seoul (KR); Young-Jin Kim, Seoul (KR); Doo-Hoon Lee, Seoul (KR); Ji-Hyun Lee, Jinhae-si (KR); Hee-Hoon Yoon, Incheon (KR); Jae-Nam Ryu, Incheon (KR); Choon-Hyuck Kwon, Seoul (KR); Jeong-Kwon Noh, Seoul (KR); Hey-Jung Park, Seoul (KR)

(73) Assignees: Lifecord Inc., Seoul (KR); Jung Keug Park, Seoul (KR); Sung Koo Kim, Busan (KR); Suk Koo Lee, Seoul (KR)

(*) Notice: Subject to any disclaimer, the term of this patent is extended or adjusted under 35 U.S.C. 154(b) by 322 days.

(21) Appl. No.: 12/593,864

(22) PCT Filed: Mar. 28, 2008

(86) PCT No.: PCT/KR2008/001759
§ 371 (c)(1), (2), (4) Date: Sep. 29, 2009

(87) PCT Pub. No.: WO2008/120918
PCT Pub. Date: Oct. 9, 2008

(65) Prior Publication Data
US 2010/0126923 A1    May 27, 2010

(30) Foreign Application Priority Data
Mar. 30, 2007  (KR) .................. 10-2007-0031590

(51) Int. Cl.
*C12M 1/14* (2006.01)
*C12M 3/04* (2006.01)

(52) U.S. Cl. ............... 435/299.1; 435/289.1; 435/297.1
(58) Field of Classification Search ............... 435/289.1, 435/295.3, 297.2–297.5, 298.2, 299.1, 297.1
See application file for complete search history.

(56) References Cited

U.S. PATENT DOCUMENTS

| | | | | |
|---|---|---|---|---|
| 4,846,786 A * | 7/1989 | Freed et al. | .................. | 604/5.01 |
| 5,084,350 A * | 1/1992 | Chang et al. | ............... | 428/402.2 |
| 5,270,192 A * | 12/1993 | Li et al. | .......................... | 435/174 |
| 5,643,794 A * | 7/1997 | Liu et al. | ..................... | 435/289.1 |
| 6,858,146 B1 | 2/2005 | Myers et al. | | |
| 2002/0168758 A1* | 11/2002 | Martinez et al. | ........... | 435/297.4 |

(Continued)

FOREIGN PATENT DOCUMENTS
KR    2002-0066507 A    8/2002
(Continued)

Primary Examiner — Michael Marcheschi
Assistant Examiner — Shanta G Doe
(74) Attorney, Agent, or Firm — Sughrue Mion, PLLC (57) ABSTRACT

The present invention discloses a bioartificial liver system comprising a fixed-bed bioreactor packed with gel beads containing hepatocytes of an animal, a plasma reservoir, a plasma separator, and an efflux chamber, wherein the plasma reservoir is located at a position higher than the bioreactor, a ventilation filter in contact with atmosphere is provided at the top of the plasma reservoir, and the top of the plasma reservoir is directly connected to the efflux chamber via a connecting line. The inventive system satisfactorily performs the essential liver functions without the problems of gel bead damage or channeling.

6 Claims, 8 Drawing Sheets

U.S. PATENT DOCUMENTS

| | | | |
|---|---|---|---|
| 2003/0228685 A1* | 12/2003 | Nyberg | 435/297.1 |
| 2004/0265997 A1* | 12/2004 | Park | 435/370 |
| 2005/0014250 A1* | 1/2005 | Galavotti | 435/297.2 |

FOREIGN PATENT DOCUMENTS

| | | |
|---|---|---|
| KR | 2006-0048546 A | 5/2006 |

* cited by examiner

FIG. 6A 1. marker
2. porcine hepatocytes
3. the sample circulating the inventive system
4. the sample circulating the conventional system
5. control sample

FIG. 6B

SEQUENCE LISTING

```
<160> NUMBER OF SEQ ID NOS: 2

<210> SEQ ID NO 1
<211> LENGTH: 22
<212> TYPE: DNA
<213> ORGANISM: Artificial Sequence
<220> FEATURE:
<223> OTHER INFORMATION: forward primer

<400> SEQUENCE: 1
gtgctgccaa ggctgtgggc aa                                            22
```

```
<210> SEQ ID NO 2
<211> LENGTH: 23
<212> TYPE: DNA
<213> ORGANISM: Artificial Sequence
<220> FEATURE:
<223> OTHER INFORMATION: reverse primer

<400> SEQUENCE: 2
tggaccatga ggtccaccac cct                                         23
```

BIOARTIFICIAL LIVER SYSTEM USING BIOREACTOR PACKED WITH GEL BEADS

FIELD OF THE INVENTION

The present invention relates to a bioartificial liver system using a bioreactor packed with gel beads containing hepatocytes of an animal.

BACKGROUND OF THE INVENTION

Liver performs over 5 hundred vital functions including detoxification of toxic substances, synthesis and secretion of bile acids or bile pigments, synthesis and metabolism of plasma protein, and metabolism of glucose and lipid. Therefore, unlike heart and kidney, it is not possible to replace such liver functions by a simple system comprising a pump or a dialysis membrane (see Mito M., Artificial Organs, 10, 214-218, 1986). Although recent liver transplantation patients have shown a high survival rate, according to the Scientific Registry of United Network for Organ Sharing, only about 10% of the registering patients can receive liver transplantation in the U.S. because of the extreme shortage of organ donors, and the number of patients who expired while waiting for a liver transplant has been rapidly increasing.

Thus, there is a dire need to develop a viable liver support device such as an artificial liver, which can be efficiently and conveniently applied to keep a patient alive and minimize the sequelae of liver failure including neurological damage during the recovery of liver functions or the regeneration of the patient's native liver, and during the waiting period for receiving liver transplantation.

Therefore, there have been conducted a number of studies on a bioartificial liver system using animal hepatocytes, which can perform various biological functions of hepatocytes (see Kamlot A. et al., Biotechnol Bioeng., 50, 382-391, 1996). Such bioartificial liver comprising hepatocytes can significantly alleviate the symptoms of hepatic failure and extend the survival period, by performing the steps of separating plasma from the blood stream of a patient, treating the plasma in a bioreactor tightly packed with hepatocytes, and returning the treated plasma to the patient. Accordingly, a viable bioartificial liver must be able to cultivate hepatocytes while maintaining their functions intact and also to have a high throughput capacity.

A hollow-fiber reactor used in kidney dialysis has been applied to a bioartificial liver system due to its well-developed technology. However, this type of reactor can accommodate only a small amount of hepatocytes, which limits the reactor's throughput capacity (see Demetriou A. A. et al., Ann. Surg., 239, 660-667, 2004).

In order to solve the above-mentioned problem, there has been reported a gel-bead type or capsule type bioreactor in which hepatocytes are packed within gel beads or capsules (see David B. et. al., Int. J. Artif. Organs., 27(4), 284-293, 2004; and Xu Q. et al., Ann. Clin. Lab. Sci., 34(1), 87-93, 2004). However, this type of fixed-bed bioreactor has several problems such as damage of fragile gel beads caused by the applied pressure for circulation and depletion of oxygen and nutrients caused by channeling, which leads to necrosis of hepatocytes.

Therefore, most of recently developed gel bead type bioreactors have been in the form of a fluidized-bed in which the gel beads move freely with the flow of the fluid in the reactor (see David B. et al., Int. J. Artif. Organs, 27(4), 284-293, 2004; M. Desille et al., Crit. Care Med., 30(3), 658-663, 2002; Y. J. Hwang et al., Transpl. Proc., 32, 2349-2351, 2000; and C. Legallais et al., Artificial Organs, 24(7), 519-525, 2000).

However, such a fluidized-bed reactor is disadvantageous in that it has a relatively larger reactor volume as compared with a fixed-bed reactor and the plasma throughput rate is unacceptably low (see M. Desille et al., Crit. Care Med., 30(3), 658-663, 2002; and Y. J. Hwang et al., Transpl. Proc., 32, 2349-2351, 2000, E. Dore et al., Therapeutic Apheresis, 3(3), 264-267, 1999). In this regard, it has been reported that considering the oxygen consumption rate of hepatocytes, a fluidized reactor having $2 \times 10^{10}$ hepatocytes needs a plasma flow rate of at least 150 ml/min in order to supply sufficient oxygen (see Florence J. et al., Biotechnol. Bioeng., 50, 404-415, 1996).

In order to overcome aforementioned problems, a gel bead type-packed upflow fixed-bed reactor has been proposed (see T. M. Rahman et al., Artificial Organs, 28(5), 476-482, 2004), but it has the problem that the throughput rate is too small for treating a hepatic failure patient.

Further, in case of a conventional downflow reactor (see F. Meuwly et al., J. Biotechnology, 122, 122-129, 2006), no damage of the packing material occurs when a disk type fibrous packing material having high strength and porosity is used as a cell holder, but the performance of this reactor may deteriorate, or efflux of the circulating fluid may occur due to the high pressure generated by the use of a tube pump.

SUMMARY OF THE INVENTION

Accordingly, it is an object of the present invention to provide a bioartificial liver system using a bioreactor packed with gel beads, which is free of such problems as damage of gel beads and channeling.

BRIEF DESCRIPTION OF DRAWINGS

The above and other objects and features of the present invention will become apparent from the following description of the invention taken in conjunction with the accompanying drawings, which respectively show.

BRIEF DESCRIPTION OF THE REFERENCE NUMERALS IN DRAWINGS

| | |
|---|---|
| 1: bioreactor | 2: plasma reservoir |
| 3: efflux chamber | 4: connecting line |
| 5: flow-rate control pump | 6: plasma separator |
| 7: patient | 8: oxygenator |
| 9: fluid level difference | 10: ventilation filter |
| 11: pneumatic detector | 12: meshes |
| 13: plasma inlet line | 14, 15: plasma outlet lines |

DETAILED DESCRIPTION OF THE INVENTION

In accordance with the present invention, there is provided a bioartificial liver system comprising a fixed-bed bioreactor packed with gel beads containing hepatocytes of an animal, a plasma reservoir, a plasma separator, and an efflux chamber, wherein the plasma reservoir is located at a position higher over the bioreactor, a ventilation filter in contact with the atmosphere is provided at the top of the plasma reservoir, and the top of the plasma reservoir is directly connected to the efflux chamber via a connecting line.

Figure 1:
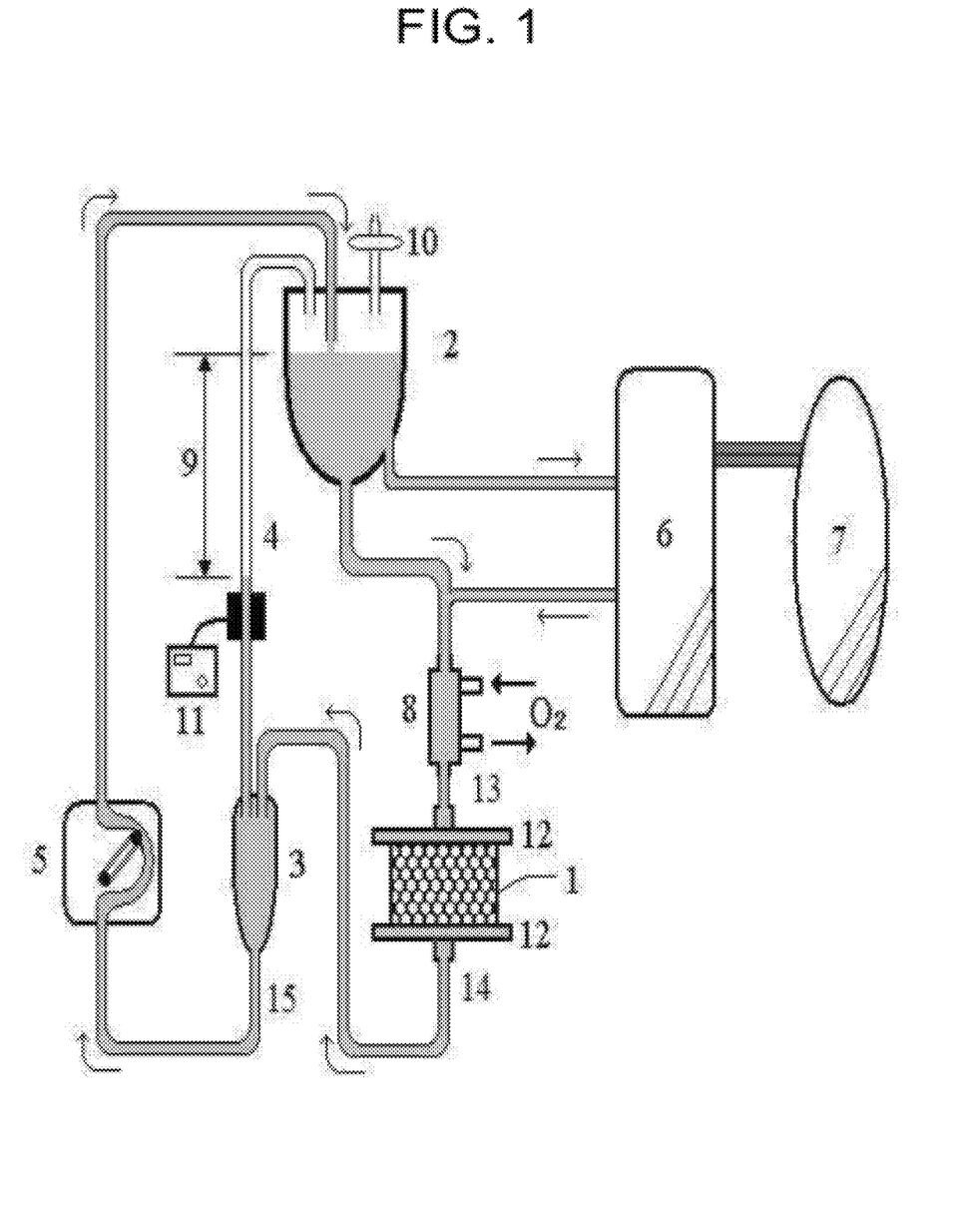
FIG. 1: a schematic diagram of the bioartificial liver system of the present invention.

Referring now to FIG. 1, the patient's blood 7 passes through plasma separator 6 to isolate the plasma to be circulated in the bioartificial liver system of the present invention. Oxygenator 8 saturates the circulating plasma with oxygen and keeps the plasma at a temperature suitable for the incubation of hepatocytes. Then, the plasma saturated with oxygen is introduced to the top of bioreactor 1 via a plasma inlet line 13.

Bioreactor packed with gel beads containing hepatocytes is one of the core elements of the inventive system for performing functions similar to a normal liver, removing toxic substances from the introduced plasma and secreting useful plasma proteins synthesized by hepatocytes. In accordance with the present invention, since the bioreactor 1 is operated in the form of a fixed-bed, its inner space is completely packed with gel beads without any void. Further, at the top and the bottom of the bioreactor 1, meshes 12 having a pore size of 50 to 500 μm are provided to retain the gel beads in the bioreactor. The meshes may be made of a biocompatible material such as stainless steel, polyester, nylon, and polyurethane.

As the hepatocytes contained in the gel beads, those separated from a pig may be used, and $5\times10^6$ to $5\times10^7$ cells may be encapsulated per 1 ml of gel beads in the form of aggregates having a diameter of 50 to 200 μm.

In the present invention, the body of the bioreactor 1 is preferred to have a volume of 100 to 1800 ml and a specific cross sectional area of 0.1 to 0.2 $cm^2$/ml to secure an efficient flow rate without creating channeling. The bioreactor 1 may be made of a polycarbonate, stainless steel or glass, and preferred is a transparent material such as polycarbonates and glass which facilitates the observation of gel beads.

In accordance with the present invention, since the plasma is introduced from the top of the bioreactor 1 and eluted from the bottom thereof, the top and the bottom of the bioreactor 1 are respectively connected to the plasma inlet line 13 and the plasma outlet line 14 provided outside the bioreactor 1.

The plasma exiting from the plasma outlet line 14 is led to the efflux chamber 3, which is connected to the upper air space of a plasma reservoir 2 via the connecting line 4 and the plasma from the efflux chamber 3 is pumped to the plasma reservoir 2 via the outlet line 15 using flow-rate control pump 5.

After the plasma flow from the efflux chamber 3 is introduced to the plasma reservoir 2 through the flow-rate control pump 5, a portion of the plasma is returned to patient 7 through the plasma separator 6 and the remaining portion is remixed with the patient 7's plasma introduced to the plasma separator 6, which is circulated again in the inventive system.

The characteristic feature of the inventive system is that, while the inner pressure of the plasma reservoir 2 is maintained at an atmospheric pressure by using the ventilation filter 10, the circulation of the plasma is driven by the pressure created by the fluid level difference 9 between the plasma retained in plasma reservoir 2 and the plasma in the connecting line 4 attached to the efflux chamber 3. Accordingly, the maximum pressure applied to the bioreactor 1 can be controlled by adjusting the length of the vertical height of the connecting line 4 (the difference 9 between the fluid level of the plasma reservoir 2 and that of the connecting line 4). The connecting line 4 may be installed in various forms such as an inclined form to meet the desired vertical height.

Considering that the preferable pressure range applied to the bioreactor 1 is 3 to 45 mmHg, the connecting line 4 is preferred to have a vertical height of 4 to 61 cm. If the pressure applied to bioreactor 1 exceeds 45 mmHg, there is a risk of gel bead breakage. Once gel beads are damaged, the animal hepatocytes contained therein are leaked into the plasma, which may induce antibody in the plasma to cause necrosis of the hepatocytes, or result in returning contaminated plasma to the patient 7 in which the contamination of the plasma may be caused by infectious microorganisms rarely present in the hepatocytes.

The flow-rate control pump 5 controls the plasma flow rate to keep the fluid level difference at a desired value. Therefore, in the inventive system, although the maximum plasma flow rate is determined by the vertical height of the connecting line 4, the circulation rate is essentially controlled by the flow-rate control pump 5. In other words, depending on the flow rate controlled by the flow-rate control pump 5, the plasma of the efflux chamber 3 fills the connecting line 4 until the flow rate of the plasma equilibrates with that of the plasma effluxed from the bioreactor 1, at which point the fluid level difference 9 is determined. Preferably, the fluid level difference 9 is 20 to 40 cm, and a fluid level difference 9 of 20 cm, for example, approximately corresponds to a plasma flow rate of 250 ml/min. In this connection, a fluid level difference 9 of 40 cm generates a pressure of about 29.4 mmHg that is applied to bioreactor 1, and in order to prevent gel bead damage, it is preferred to keep the fluid level difference 9 at a value not more than 40 cm.

Further, in the inventive system, in case that the weakened beads obstruct the passages of plasma, or other unexpected problems occur in the bioreactor 1, the resulting pressure variation causes the plasma level change in the connecting line 4 followed by the change in the fluid level difference 9, and thus, any variation in the plasma pressure can be immediately detected. Specifically, such pressure variation can be checked in real time by using pneumatic detector 11 installed on the connecting line 4.

According to the inventive system, since plasma is circulated through the bioreactor 1 from the top to the bottom by the pressure difference created by the fluid level difference 9, channeling or gel bead damage does not occur. In addition, the inventive system provides a stable and effective flow rate, and exhibits excellent performance characteristics in removing toxins from plasma and providing necessary proteins. Therefore, it is very useful as a liver support device.

The following Examples are given for the purpose of illustration only, and are not intended to limit the scope of the invention.

EXAMPLE

Preparation of the Bioartificial Liver System According to the Present Invention 1) Isolation and Cultivation of Porcine Hepatocytes A large amount of hepatocytes were isolated from a pig using a conventional procedure (see Sielaff T. D. et al., *Transplantation*, 27, 1459-63, 1995) as follows.

A 10 kg crossbred boar (Landrace×Yorkshire×Duroc, Medi-pig Korea, Chun-An, Korea) was made to fast overnight with an access to water. The boar was anesthetized with ketamine (20 mg/kg, Yuhan Corporation) and xylazine (2 mg/kg, Bayer Korea, Ltd.), followed by subjecting to inhalation of enflurane (Choongwae Pharma corporation) through endotracheal intubation, and, then, nocuron (muscle relaxant, 0.1 mg/kg, Hanwha Pharma) was injected. After cutting open the abdomen, a tube was connected to the portal vein.

The liver was perfused with a first perfusion solution (NaCl 8 g/l, KCl 0.4 g/l, $NaH_2PO_4.2H_2O$ 0.078 g/l, $Na_2HPO_4.12H_2O$ 0.151 g/l, HEPES (4-(2-hydroxyethyl)-1-piperazineethane-sulfonic acid, Sigma Chem Co.) 2.38 g/l, EDTA (ethylenediamine tetraacetic acid, Gibco BRL Co.) 0.19 g/l, sodium bicarbonate 0.35 g/l, glucose 0.9 g/l, penicillin 100 unit/ml, streptomycin 10 mg/ml and amphotericin B 25 μg/ml), and the liver thus treated was removed.

The resulting liver, placed on a clean bench was perfused again with a second perfusion solution (collagenase (Gibco BRL) 0.5 g/l, trypsin inhibitor (Gibco BRL) 0.05 g/l, NaCl 8 g/l, KCl 0.4 g/l, $CaCl_2$ 0.56 g/l, $NaH_2PO_4.2H_2O$ 0.078 g/l, $Na_2HPO_4.12H_2O$ 0.151 g/l, HEPES 2.381 g/l, sodium bicarbonate 0.35 g/l, penicillin 100 unit/ml, streptomycin 10 mg/ml and amphotericin B 25 μg/ml), while providing the liver with sufficient oxygen with an artificial heart-lung machine (CapioxSX-10, Terumo, Japan) and maintaining the perfusion solution at 37° C. and the perfusion rate at not less than 700 ml/min.

The liver capsule as well as the remaining tissues were eliminated, and then, $2.0 \times 10^{10}$ hepatocytes were isolated by washing after repeating centrifugation (four times, each time for 2 min at 500 rpm).

A portion of the hepatocytes thus obtained was taken to test the cell viability in accordance with the trypan blue dye exclusion method. As a result, 89% cell viability was measured.

The isolated hepatocytes were added to 1 L of a suspension culture medium (Williams' E medium containing insulin 5 mg/l, albumin 0.1% and epithelial cell growth factor 20 μg/ml, Sigma Chemical Company) placed in a spinner flask to a concentration of $1.5 \times 10^6$ cells/ml, and the resulting suspension was cultured for 10 to 20 hours. When the cultured hepatocytes formed hepatocyte aggregates having a mean diameter of 70 μm, the aggregates were recovered from the culture medium.

2) Manufacture of Hepatocyte-Containing Gel Beads

Figure 3:
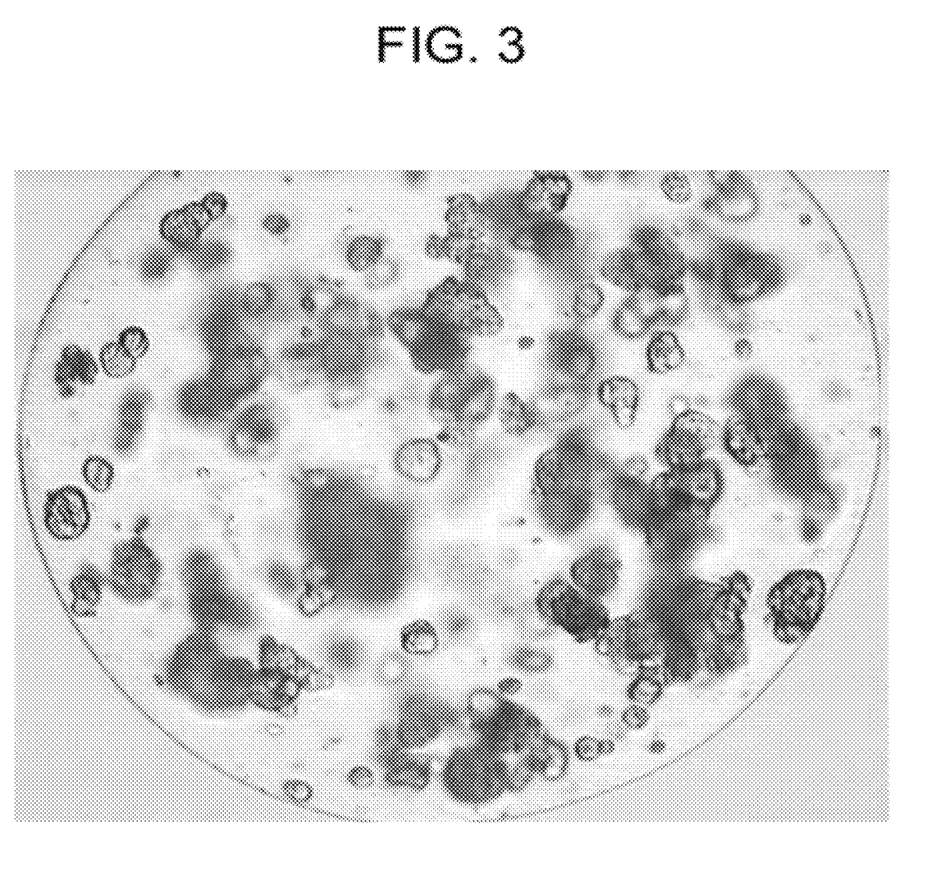
FIG. 3: a microscopic picture of alginate gel beads containing aggregates of hepatocytes.

The hepatocyte aggregates recovered in step 1) (total number of hepatocytes: $2 \times 10^{10}$, 100 ml) were mixed with 1.5% alginate solution (500 ml), and the resulting mixture was added dropwise to 100 mM $CaCl_2$ solution using a multiple nozzle injector to form gel beads. The gel beads were washed four times with Williams' E medium to eliminate residual calcium ion. As shown in FIG. 3, the resulting gel beads had a mean diameter of 1.1 mm as was confirmed by microscopy.

3) Manufacture of the Inventive Bioartificial Liver System

The bioartificial liver system of the present invention illustrated in FIG. 1 was manufactured by packing the hepatocyte-containing gel beads obtained in step 2) in a bioreactor having a volume of 550 ml. In this case, the length of the connecting line 4 was adjusted to 40 cm.

Experimental Example 1

In Vitro Performance Test of the Inventive Bioartificial Liver System

In order to simulate the treatment of an actual hepatic failure patient, the bioartificial liver system of the present invention was supplied with a suspension culture medium (Williams' E medium containing insulin 5 mg/l, albumin 0.1% and epithelial cell growth factor 20 μg/ml, Sigma Chemical Company) containing 1300 μg/dl ammonia (exaggerated condition) for the initial 7 hours, and, subsequently, with a suspension culture medium containing 420 μg/dl ammonia (the level observed in an actual hepatic failure case) for 4 hours, wherein the feed rate of each medium was set at 6 ml/min.

Figure 4:
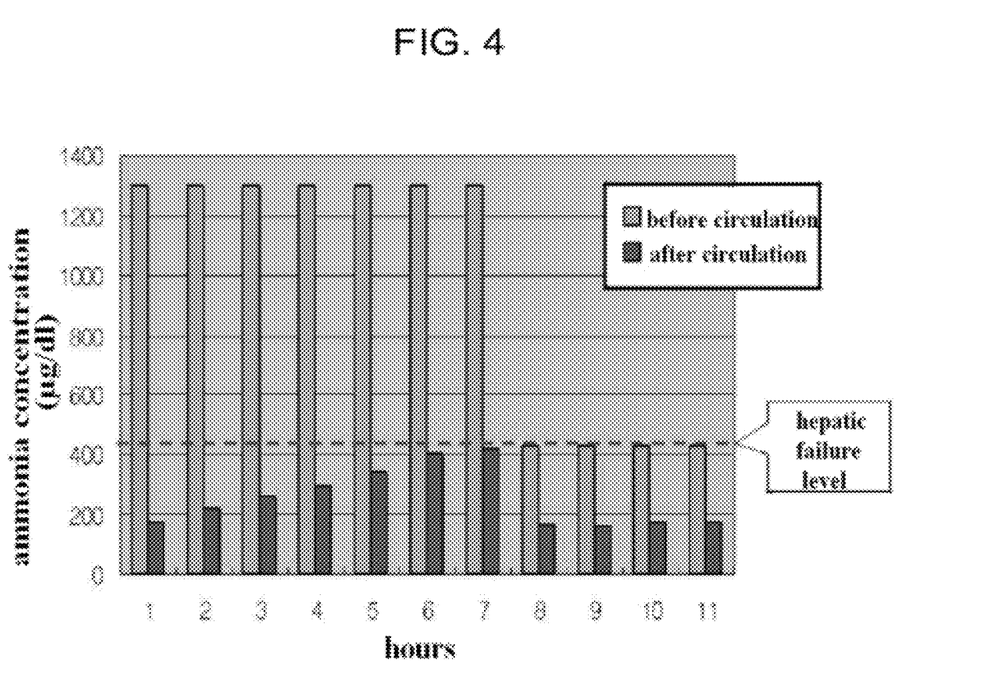
FIG. 4: the results of in vitro performance test using the bioartificial liver system of the present invention.

The results in FIG. 4 show that after such treatment, about 77% of ammonia was removed from the medium, and such a high detoxifying capacity remained unchanged even after 11 hours.

Experimental Example 2

Performance Test for the Liver-Assisting Function Using a Hepatic Failure Pig

A shoat weighing about 50 kg (available as an international experimental animal, 3 to 4 months old) was systemically anesthetized and subjected to endotracheal intubation, followed by securing blood vessel for collecting blood sample. Anesthesia was maintained by subjecting the animal to inhalation of enflurane (Choongwae Pharma Corporation).

After cutting open the abdomen of the anesthetized shoat, the infrahepatic inferior vena cava and portal vein were connected in the way of side-to-side anastomosis to bypass the blood stream to the jugular vein, thereby inducing hepatic failure.

A double lumen catheter was inserted into the jugular vein of the hepatic failure-induced shoat and connected to the plasma separator (6, Cobe Spectra, Gambro BCT, USA) of the inventive bioartificial liver system.

Operating conditions were as follows:

Blood circulating rate within the plasma separator: 90 ml/min

Flow rate of the plasma separated from the blood and existed the plasma separator: 40 ml/min Circulation rate through the bioreactor: 250 ml/min Fluid level difference: 20 cm After starting the operation the system, hourly blood samples were collected from the artery to measure the blood ammonia concentration (test group). The same procedure was repeated with control groups: as hepatic failure-induced pigs connected to no bioartificial liver system (control group for hepatic failure); as those connected to a bioartificial liver system where hepatocytes were not packed in the bioreactor (control group for bioreactor). Further, the survival time of the pig in each group was determined.

Figure 5A:
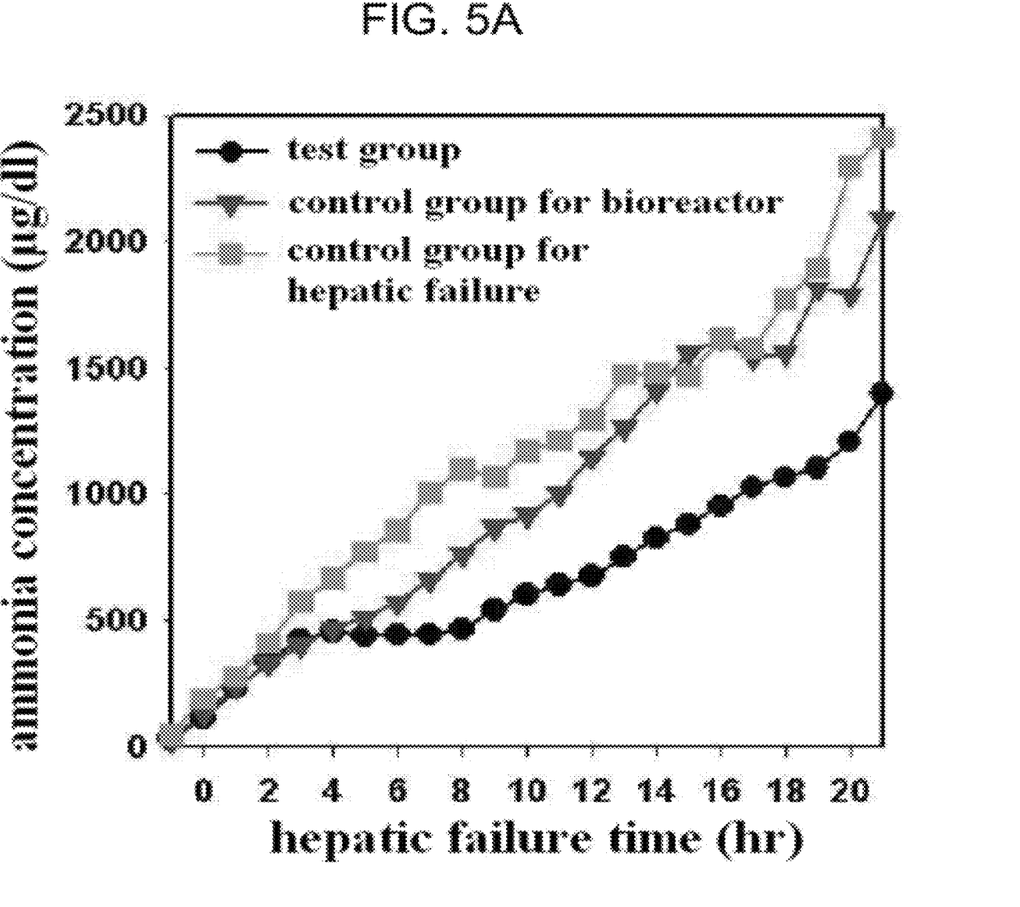
FIG. 5A: time dependent changes in the blood ammonia concentration of hepatic failure induced pigs observed for the cases of using: no bioartificial liver system (control group for hepartic failure); a bioartificial liver system where hepatocytes are not packed within its bioreactor (control group for bioreactor); and the bioartificial liver system of the present invention (test group), respectively.
Figure 5B:
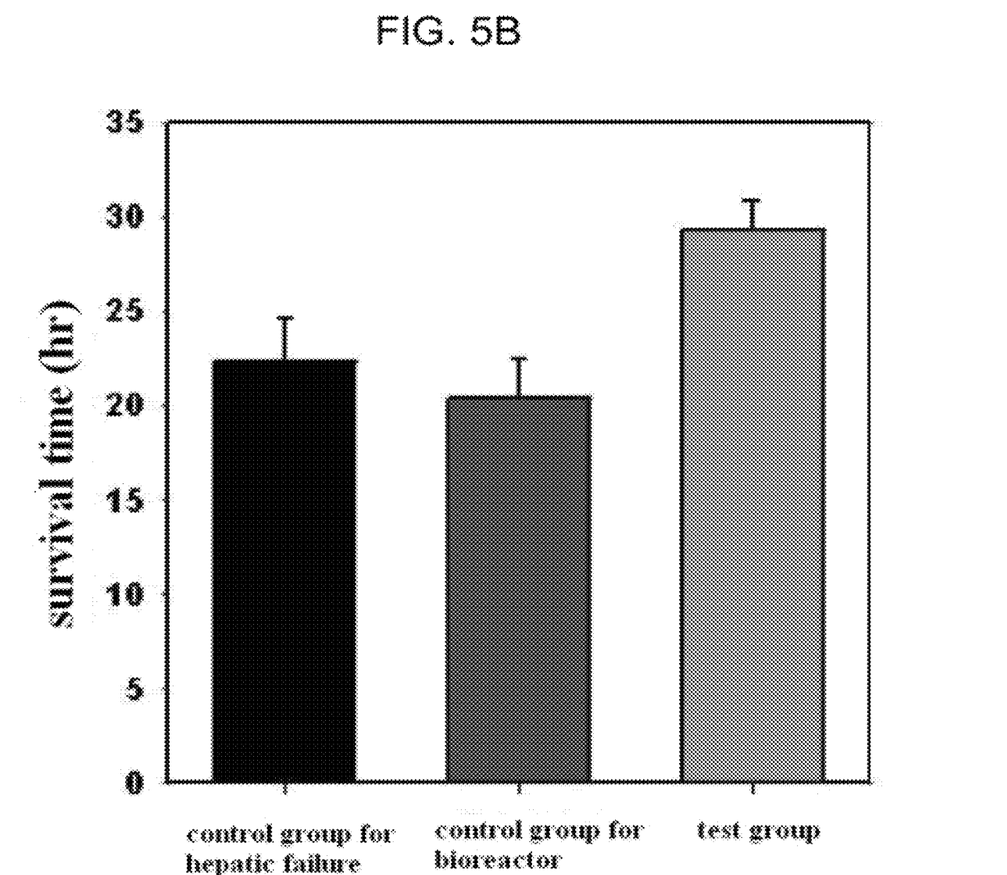
FIG. 5B: survival times of hepatic failure induced pigs observed for the cases of using: no bioartificial liver system (control group for hear failure); a bioartificial liver system where hepatocytes are not packed within its bioreactor (control group for bioreactor); and the bioartificial liver system of the present invention (test group), respectively.

As shown in FIGS. 5A and 5B, the blood ammonia concentration observed for the test group using the inventive bioartificial liver system was remarkably lower than those of the control groups, and the survival time of the test group was extended by about 7.5 hours as compared to the control groups. Accordingly, it was confirmed that the inventive bioartificial liver system is useful for the recovery or life extension of acute hepatic failure patents.

Experimental Example 3

Comparison of Gel Bead Damage Between the Inventive Bioartificial Liver System and a Conventional One In order to verify the superior stability of the inventive bioartificial liver system, a bioartificial liver system was manufactured in the same way as described in the above Example, except that the volume of a bioreactor 1 was changed to 260 ml.

Figure 2:
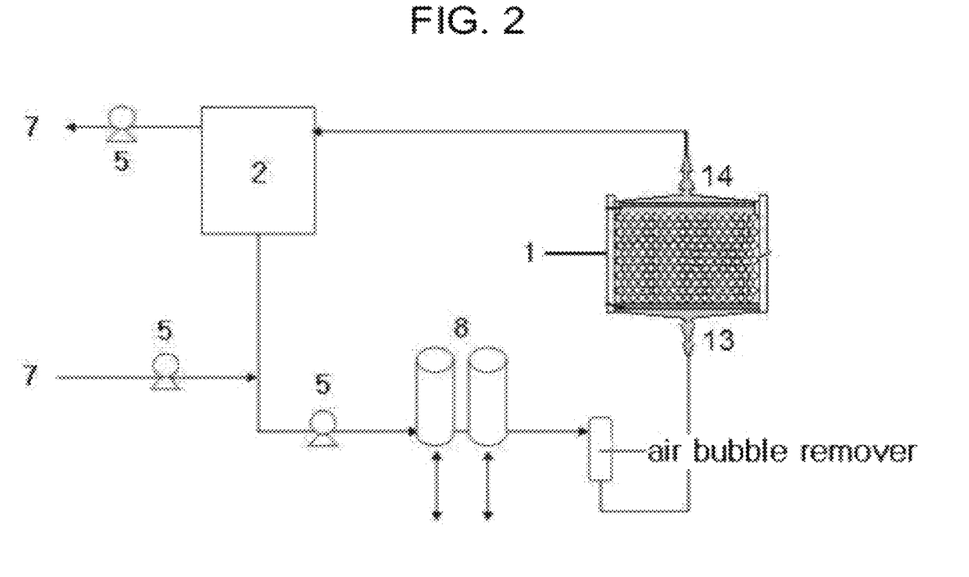
FIG. 2: a schematic diagram of the conventional upflow fixed-bed bioartificial liver system disclosed in Korean Patent Laid-open Publication No. 2006-48546.

Meanwhile, a comparative system as illustrated in FIG. 2 was manufactured in accordance with the conventional method (see Korean Patent Laid-open Publication No. 2006-48546) by: packing hepatocytes-containing gel beads which had been manufactured as described in steps 1) and 2) of the above Example in a bioreactor having a volume of 260 ml; adjusting the upper plate of the bioreactor to compress the upper level of the naturally precipitated gel beads by 20%; and circulating the plasma from the bottom to the top of the bioreactor by using a tube pump.

A test solution was obtained by mixing the porcine plasma recovered from the inventive bioartificial liver system after conducting the Experimental Example 2 with a suspension culture medium having the same constitution as used in Experimental Example 1, in a volume ratio of 2:1.

The test solution was circulated through each system at a flow rate of 300 ml/min. In the inventive system, the fluid level difference between the plasma filled in the connecting line and that of the plasma reservoir was maintained at 40 cm.

15 ml of each test solution was taken every 2 hour, while circulating the test solution through each system under the above-mentioned conditions for 6 hours, centrifuged at 3000 rpm for 10 min to eliminate supernatant, and trypan blue was added thereto to a total volume of 100 μl.

Each solution thus obtained was transferred onto a glass concave slide, and the total cell number was measured with a microscope.

The results are shown in Table 1.

TABLE 1

| Perfusion time (hr) | Cell number per 15 ml | |
|---|---|---|
| | Comparative system (a conventional fixed-bed bioreactor) | Inventive system (a bioreactor where perfusion is driven by fluid level difference) |
| 0 | 2 | 3 |
| 2 | 9 | 2 |
| 4 | 20 | 1 |
| 6 | 21 | 2 |

As presented in Table 1, in the comparative system, the number of hepatocytes leaked out of the gel beads markedly increased after 4 hours circulation, whereas, for the inventive system, the number of freed cells still remained unchanged even after 6 hours of circulation.

Further, a 50 ml sample was collected from each of the two bioreactor after 6 hours circulation and centrifuged at 4,000 rpm at 4° C., and genomic DNA (gDNA) was extracted from the cells isolated from each sample using DNeasy Kit (QIAGEN GmbH, Hilden, Germany).

PCR analysis was performed using the DNA thus extracted as a template, and a forward primer (SEQ ID NO: 1) and a reverse primer (SEQ ID NO: 2) for GAPDH gene, the housekeeping gene. As a control, the initial test solution was analyzed in the same way.

Figure 6A:
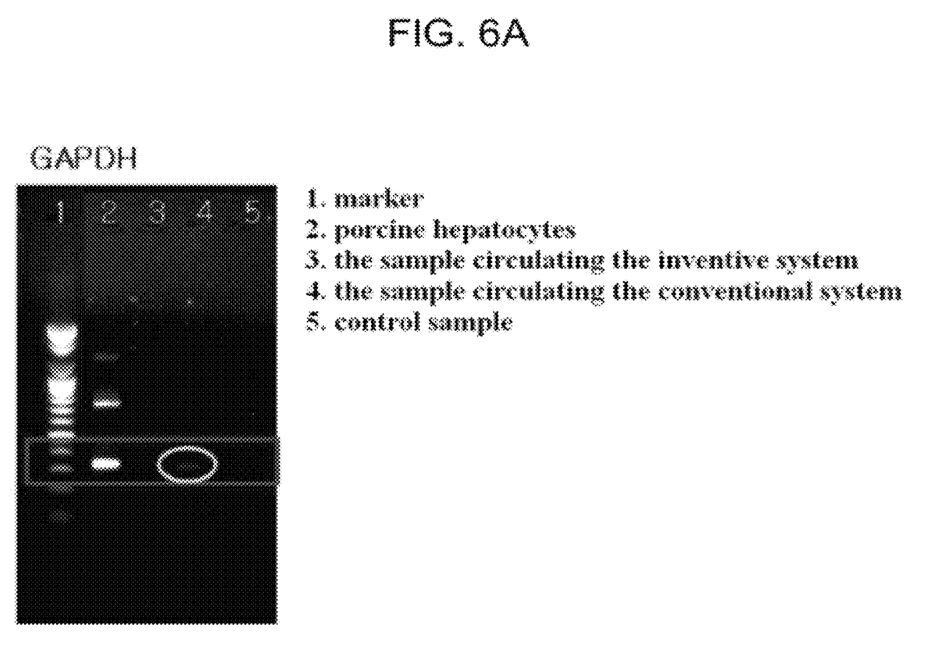
FIG. 6A: a picture showing the PCR analysis results in order to check whether gel beads are damaged in the bioartificial liver system of the present invention or in the conventional upflow fixed-bed one by detecting the presence of GAPDH gene in the circulating fluid.

As shown in FIG. 6A, no cells were detected in the sample circulating the inventive system, whereas the presence of cells was detected in the sample circulating the comparative system.

Figure 6B:
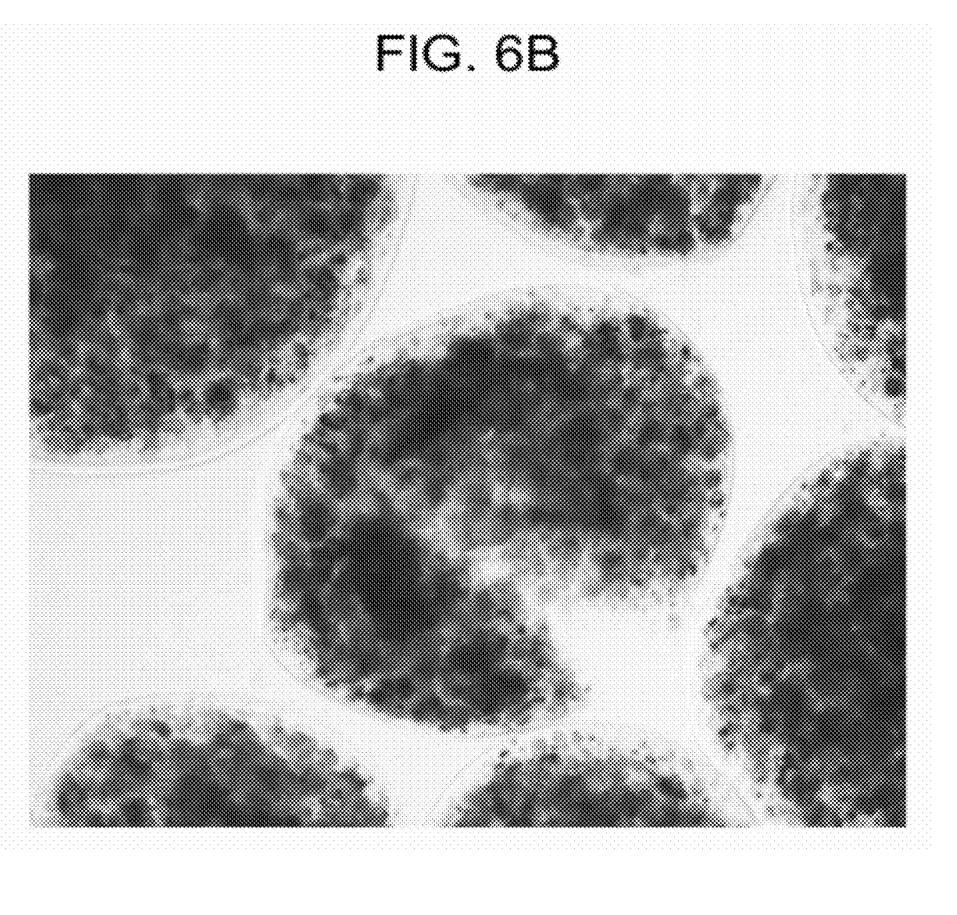
FIG. 6B: a picture showing damaged beads after using the conventional upflow fixed-bed bioartificial liver system disclosed in Korean Patent Laid-open Publication No. 2006-48546.

Meanwhile, after the above experiments, 5 ml of gel beads were recovered from each bioreactor of the inventive and comparative systems. According to microscopic examinations, no damage of the gel beads of the inventive system was observed, whereas considerate damage of about 150 gel beads in total, was observed for the gel beads of the comparative system (FIG. 6B).

Consequently, it was confirmed that the inventive system efficiently prevents hepatocytes from leaking out of gel beads in contrast to the conventional upflow fixed-bed system.

While the invention has been described with respect to the above specific embodiments, it should be recognized that various modifications and changes may be made to the invention by those skilled in the art which also fall within the scope of the invention as defined by the appended claims.

What is claimed is:

1. A bioartificial liver system comprising
a fixed-bed bioreactor packed with gel beads containing hepatocytes of a mammal,
a plasma reservoir which is in fluid communication with the bioreactor,
a plasma separator which separates plasma from blood and supplies the plasma to the bioreactor,
an efflux chamber which receives the plasma from the bioreactor and is equipped with (i) a first connecting line connecting the efflux chamber to the top of the plasma reservoir for supplying the plasma from the efflux chamber to the plasma reservoir, and (ii) a second connecting line which connects the efflux chamber and the upper air space of the plasma reservoir and has a vertical height of 4 to 61 cm, and
a ventilation filter which is in contact with atmosphere and is provided at the top of the plasma reservoir,
wherein the bioreactor receives plasma from the plasma separator and from the plasma reservoir,
wherein the plasma reservoir is located at a position higher than the bioreactor and supplies the plasma received from the efflux chamber to the plasma separator and to the bioreactor, and
wherein the pressure applied to the bioreactor is 3 to 45 mmHg.

2. The bioartificial liver system of claim 1, wherein the bioreactor comprises meshes having a pore size of 50 to 500 μm at the top and the bottom thereof.

3. The bioartificial liver system of claim 1, wherein the gel beads contain porcine hepatocytes.

4. The bioartificial liver system of claim 1, wherein the gel beads contain $5 \times 10^6$ to $5 \times 10^7$ hepatocytes per milliliter.

5. The bioartificial liver system of claim 1, wherein the hepatocytes contained in the gel beads are in the form of an aggregate having a diameter of 50 to 200 μm.

6. The bioartificial liver system of claim 1, wherein the bioreactor has a volume of 100 to 1800 ml and a specific cross sectional area of 0.1 to 0.2 cm$^2$ per milliliter of the reactor volume.

* * * * *